(12) United States Patent
Chi et al.

(10) Patent No.: US 7,915,414 B2
(45) Date of Patent: Mar. 29, 2011

(54) BLUE-EMITTING ORGANOMETALLIC COMPLEXES AND THEIR APPLICATION

(75) Inventors: Yun Chi, Hsinchu (TW); Cheng-Han Yang, Pingtung County (TW); Pi-Tai Chou, Taipei (TW); Chung-Chih Wu, Taipei (TW); Chih-Hao Chang, Taipei (TW)

(73) Assignee: Yun Chi, Hsinchu (TW)

( * ) Notice: Subject to any disclaimer, the term of this patent is extended or adjusted under 35 U.S.C. 154(b) by 582 days.

(21) Appl. No.: 11/933,855

(22) Filed: Nov. 1, 2007

(65) Prior Publication Data
US 2008/0125591 A1 May 29, 2008

Related U.S. Application Data

(60) Provisional application No. 60/860,808, filed on Nov. 24, 2006.

(51) Int. Cl.
C07F 15/00 (2006.01)
H01L 51/50 (2006.01)

(52) U.S. Cl. ............ 546/2; 428/690; 428/689; 313/504; 546/10

(58) Field of Classification Search ............. 546/2, 10; 428/690, 689; 313/504
See application file for complete search history.

(56) References Cited

FOREIGN PATENT DOCUMENTS
JP 2002203681 A * 7/2002

OTHER PUBLICATIONS

Sasaki, I. et al.: Facile synthesis of cyclometalated Ruthenium complexes with substituted phenylpyridines. Eur. J. Inorg. Chem., vol. 16, pp. 3294-3302, Aug. 2006.*
Ryabov, A.D. et al.: Low-Potential cyclometalated Osmium(II) mediators of glucose oxidase. Inorg. Chem., vol. 42, pp. 6598-6600, 2003.*

* cited by examiner

*Primary Examiner* — Charanjit S Aulakh
(74) *Attorney, Agent, or Firm* — Wpat, PC; Justin King

(57) ABSTRACT

The present invention discloses organometallic complexes with transition metal elements and their application in fabrication of a variety of light-emitting devices. The mentioned organometallic complexes can serve as emitting material or dopant for blue phosphorescent organic light-emitting devices with excellent performance. The mentioned organometallic complexes have a general formula as the following:

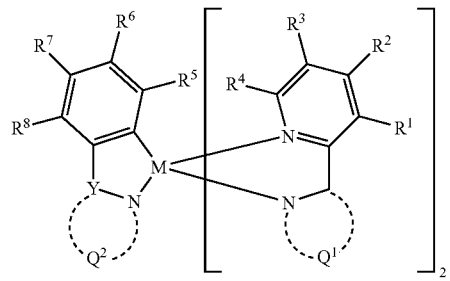

Wherein M represents a transition metal element, and $Q^1$ and $Q^2$ respectively represent an atomic group forming a nitrogen-containing heterocyclic ring as a five member ring, a six member ring, or a seven member ring.

22 Claims, 4 Drawing Sheets

BLUE-EMITTING ORGANOMETALLIC COMPLEXES AND THEIR APPLICATION

BACKGROUND OF THE INVENTION

1. Field of the Invention

The present invention is generally related to luminescent transition metal complexes, and more particularly to blue-emitting organometallic complexes and their application.

2. Description of the Prior Art

Phosphorescent organic light emitting diodes (OLEDs) are under intensive investigation because of their potential of achieving improved device performances. The electrophosphorescence are easily generated from both singlet and triplet excited states and, thus, their internal quantum efficiency can reach a theoretical level of unity, rather than the 25% inherent upper limit imposed by the formation of singlet excitons for their fluorescent counterparts. Thus, a great deal of effort has been spent on the third-row transition metal complexes, for developing highly efficient phosphors that can emit all three primary colors: red, green and blue. Despite of the elegant research on both red and green phosphors, there are only scatter reports on the room temperature blue phosphors. The best known example is one Ir(III) complex named FIrpic (as shown in FIG. 1) which has proved to be an excellent dopant for sky-blue phosphorescent OLEDs. Further improvements were made by substituting picolinate with other ancillary ligands such as pyridyl azolate to afford FIrtaz (as shown in FIG. 1) and even employing a combination of cyanide and phosphine. These modifications have produced a hypsochromic shift of ~10 nm versus the emission of FIrpic. However, significant lowering of quantum efficiency was noted in some cases, which have hampered the fabrication of the true-blue phosphorescent OLEDs. Therefore, new blue light-emitting materials are still needed corresponding to increasing phosphorescent performance and practical operation durability.

SUMMARY OF THE INVENTION

According to the above, the present invention provides new organometallic complexes to fulfill the requirements of this industry.

One object of the present invention is to provide organometallic complexes display highly efficient blue phosphorescence at room temperature and are with high quantum efficiency.

Another object of the present invention is to provide organometallic complexes comprise two pyridyl-azolate ligands, wherein the pyridyl moiety of the mentioned ligand can comprise an electron-donating group and the azolate moiety of the mentioned ligand can comprise an electron-withdrawing group, so as to increase the blue phosphorescence of the organometallic complexes.

Another object of the present invention is to employ organometallic complexes as light-emitting materials for blue phosphorescent OLEDs. For the blue phosphorescent OLEDs, by selecting the heteroleptic coordination arrangement, the excitation is equally spread among the degenerate states of multiple chromophores.

According to above-mentioned objectives, the present invention discloses an organometallic complex. The mentioned organometallic complex has a general formula as the following:

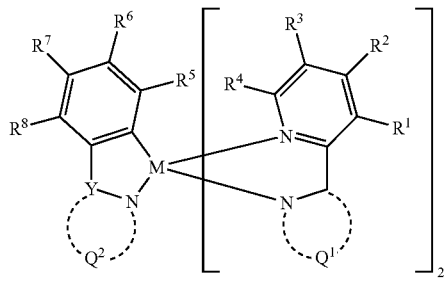

In the mentioned formula, M represents a transition metal selected from the group consisting of ruthenium, rhodium, tungsten, rhenium, osmium, iridium, and platinum. $Q^1$ and $Q^2$ respectively represent an atomic group forming a nitrogen-containing heterocyclic ring. The mentioned nitrogen-containing heterocyclic ring formed with $Q^1$ and $Q^2$ can be a five member ring, a six member ring, or a seven member ring, respectively. $R^1$, $R^2$, $R^3$, $R^4$, $R^5$, $R^6$, $R^7$, and $R^8$ in the above structure can be identical or different substituents.

DESCRIPTION OF THE PREFERRED EMBODIMENTS

Figure 1:
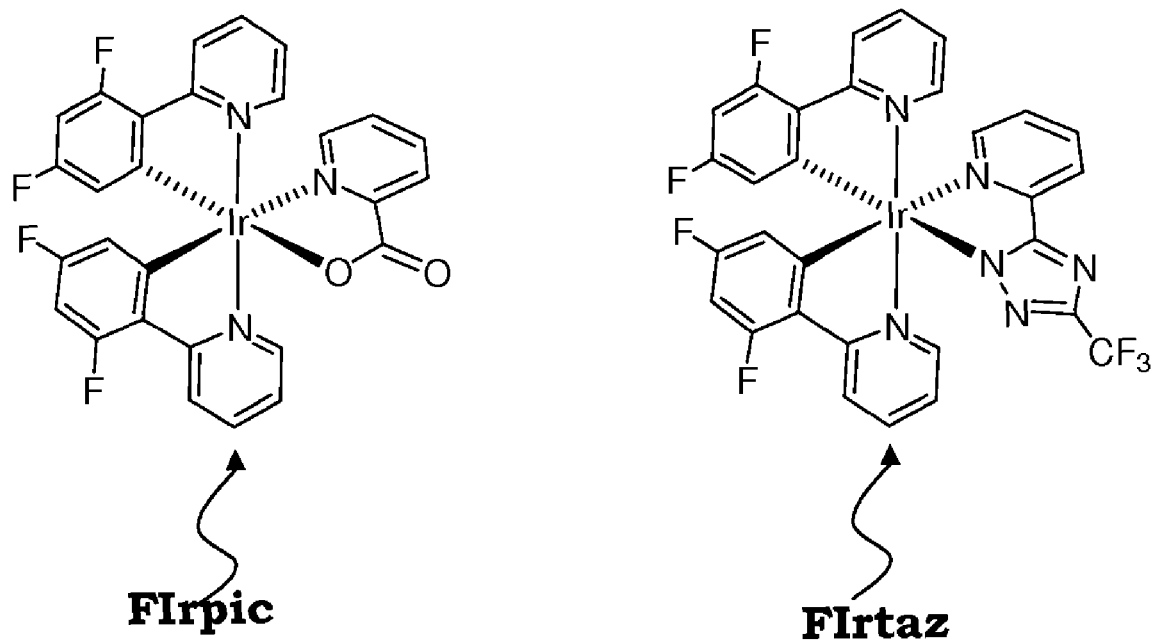
FIG. 1 shows the structural illustration of FIrpic and FIrtaz.
Figure 2:
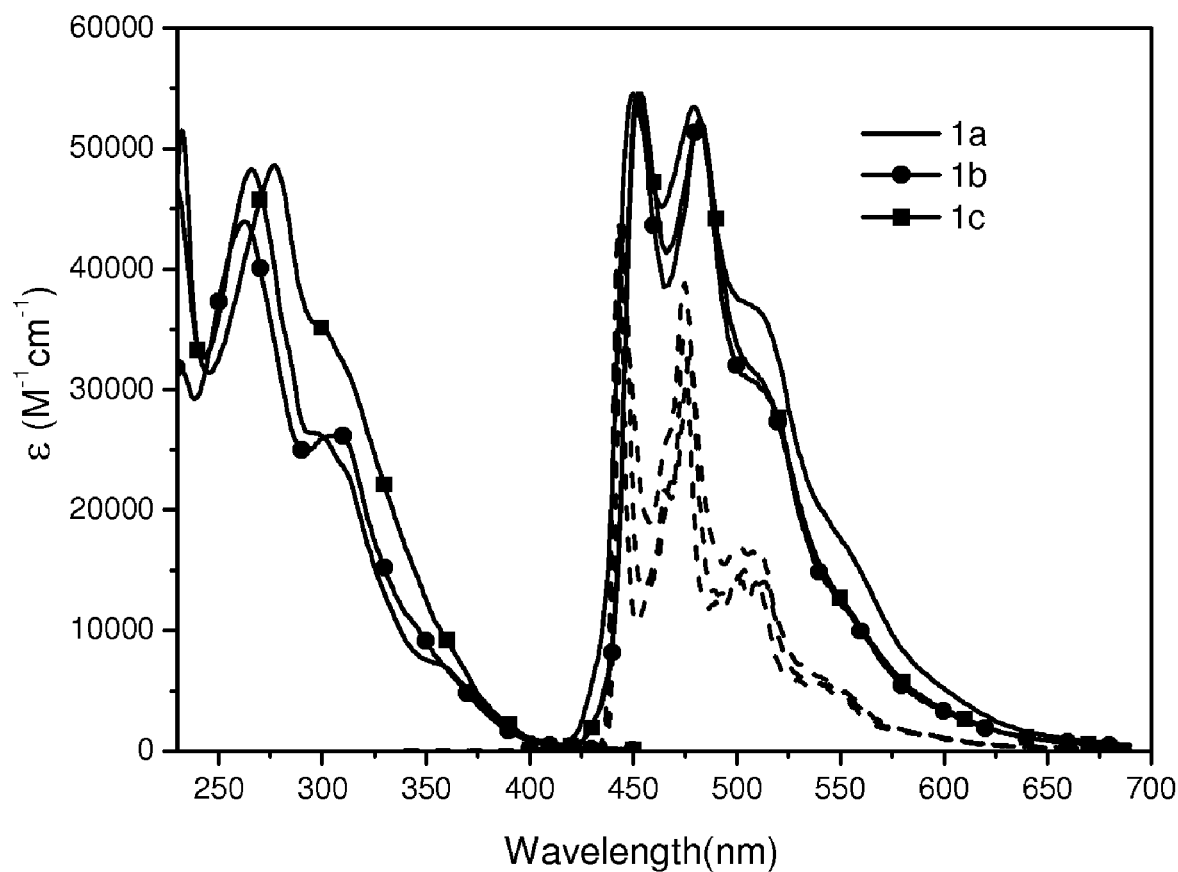
FIG. 2 shows the UV-Visible absorption and emission spectra of both isomeric heteroleptic Ir(III) complexes 1a-1b and 1c in $CH_2Cl_2$.
Figure 3:
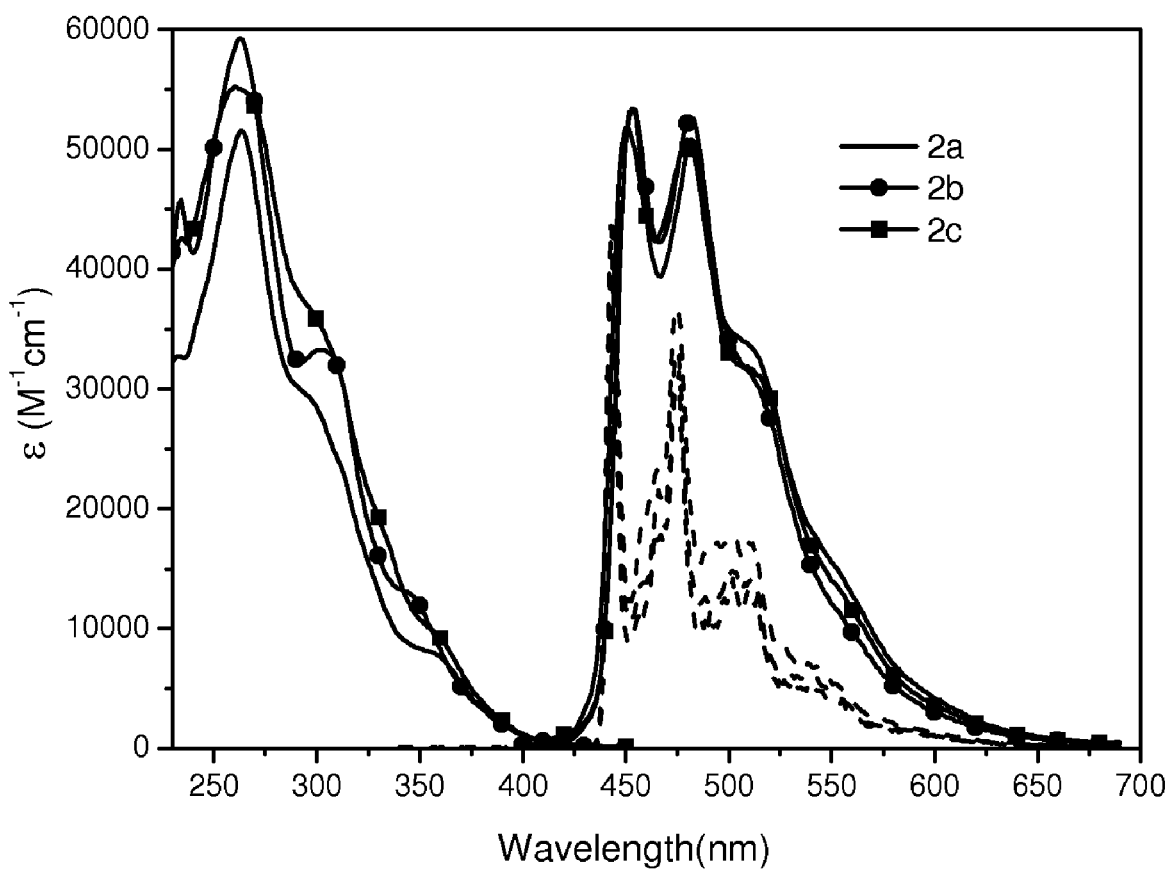
FIG. 3 shows the emission spectra of both isomeric heteroleptic Ir(III) complexes 2a-2b and 2c in $CH_2Cl_2$.

What is probed into the invention is organometallic complexes and their application. Detail descriptions of the structure and elements will be provided in the following in order to make the invention thoroughly understood. Obviously, the application of the invention is not confined to specific details familiar to those who are skilled in the art. On the other hand, the common structures and elements that are known to everyone are not described in details to avoid unnecessary redundancy. Some preferred embodiments of the present invention will now be described in greater detail in the following examples. However, it should be recognized that the present invention can be practiced in a wide range of other embodiments besides those have explicitly described, that is, this invention can also be applied extensively to other embodiments, and the scope of the present invention is not limited to those specified in the accompanying claims.

One preferred embodiment of the present invention discloses an organometallic complexes with a general formula as the following.

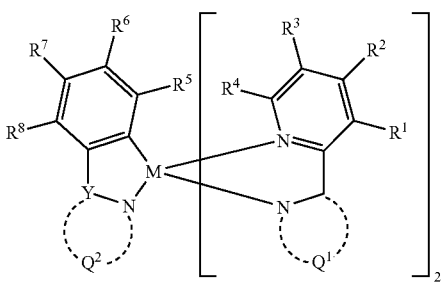

In the mentioned structure, M represents a transition metal selected from the group consisting of ruthenium, rhodium, tungsten, rhenium, osmium, iridium, and platinum. Y is selected from the group consisted of C, and N. $Q^1$ and $Q^2$ respectively represent an atomic group forming a nitrogen-containing heterocyclic ring. The atoms of the atomic group of $Q^1$ and $Q^2$ are respectively selected from the group consisted of: C, N, P, O, and S. According to this embodiment, the nitrogen-containing heterocyclic ring formed with $Q^1$ and $Q^2$ are selected from the group consisted of: a five member ring, a six member ring, a seven member ring, respectively.

In one preferred example of this embodiment, the nitrogen-containing heterocyclic ring formed with $Q^1$ and $Q^2$ can further comprise at least one substituent, and the mentioned substituent is selected from the group consisted of: hydrogen atom, halide atom, alkyl moiety, alkenyl moiety, halo-alkyl moiety, alkoxyl moiety, aromatic moiety, hetero-aromatic moiety, amino moiety, acyl moiety, ester moiety, amide moiety, cyano moiety, nitro group, aryl moiety.

According to this embodiment, $R^1$, $R^2$, $R^3$, $R^4$, $R^5$, $R^6$, $R^7$, and $R^8$ in the above structure can be identical or different, and $R^1$, $R^2$, $R^3$, $R^4$, $R^5$, $R^6$, $R^7$, and $R^8$ are respectively selected from the group consisting of a hydrogen atom, halide atom, alkyl moiety, alkenyl moiety, halo-alkyl moiety, alkoxyl moiety, aromatic moiety, hetero-aromatic moiety, amino moiety, acyl moiety, ester moiety, amide moiety, cyano moiety, nitro group, aryl moiety, tri-alkylsilyl moiety, tri-aryl silyl moiety.

In one preferred example of this embodiment, at least one of $R^1$-$R^2$, $R^2$-$R^3$, $R^3$-$R^4$, $R^5$-$R^6$, $R^6$-$R^7$, and $R^7$-$R^8$ represent an atomic group forming a ring. The above-mentioned ring(s) can be selected from the group consisted of: aromatic ring, hetero-aromatic ring, cyclic alkene, and hetero-cyclic alkene. And, the above-mentioned ring(s) can be formed as a five member ring, a six member ring, or a seven member ring. The other substituents of $R^1$~$R^8$, wherein the substituents are not used to form a ring, are identical or different, and respectively are selected from the group consisting of: hydrogen atom, halide atom, alkyl moiety, alkenyl moiety, halo-alkyl moiety, alkoxyl moiety, aromatic moiety, hetero-aromatic moiety, amino moiety, acyl moiety, ester moiety, amide moiety, cyano moiety, nitro group, aryl moiety, tri-alkylsilyl moiety, tri-aryl silyl moiety. In this example, the above-mentioned ring formed with one of $R^1$-$R^2$, $R^2$-$R^3$, $R^3$-$R^4$, $R^5$-$R^6$, $R^6$-$R^7$, and $R^7$-$R^8$ can further comprise at least one substituent, and the substituent(s) can be respectively selected from the group consisted of: hydrogen atom, halide atom, alkyl moiety, alkenyl moiety, halo-alkyl moiety, alkoxyl moiety, aromatic moiety, hetero-aromatic moiety, amino moiety, acyl moiety, ester moiety, amide moiety, cyano moiety, nitro group, aryl moiety, tri-alkylsilyl moiety, tri-aryl silyl moiety.

One preferred example of this embodiment discloses an organometallic complex represented by the following formula:

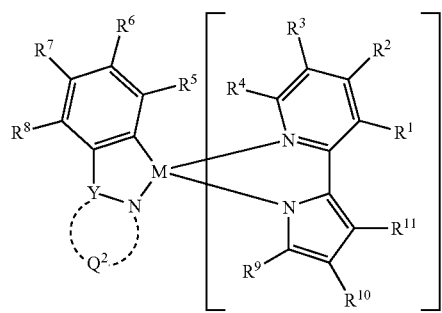

In the above structure, $R^9$, $R^{10}$, and $R^{11}$ are identical or different, and $R^9$, $R^{10}$, and $R^{11}$ are respectively selected from the group consisting of a hydrogen atom, halide atom, alkyl moiety, alkenyl moiety, halo-alkyl moiety, alkoxyl moiety, aromatic moiety, hetero-aromatic moiety, amino moiety, acyl moiety, ester moiety, amide moiety, cyano moiety, nitro group, aryl moiety.

In another preferred example of this embodiment, an organometallic complex is disclosed as the following formula:

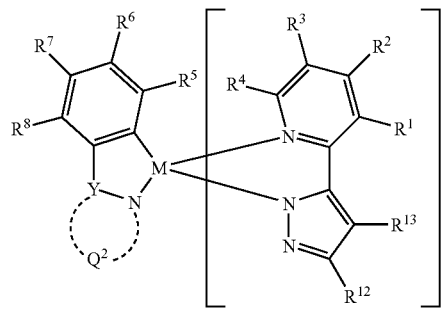

In the above structure, $R^{12}$, and $R^{13}$ are identical or different, and $R^{12}$, and $R^{13}$ are respectively selected from the group consisting of a hydrogen atom, halide atom, alkyl moiety, alkenyl moiety, halo-alkyl moiety, alkoxyl moiety, aromatic moiety, hetero-aromatic moiety, amino moiety, acyl moiety, ester moiety, amide moiety, cyano moiety, nitro group, aryl moiety.

In still another preferred example of this embodiment, an organometallic complex is represented by the following formula:

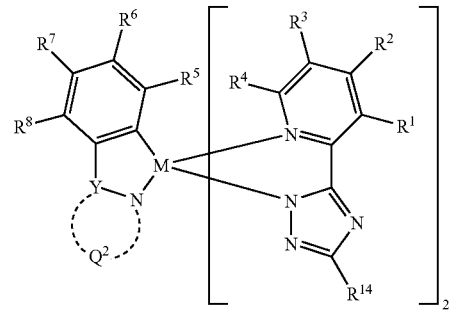

In the above structure, $R^{14}$ is selected from the group consisting of a hydrogen atom, halide atom, alkyl moiety, alkenyl moiety, halo-alkyl moiety, alkoxyl moiety, aromatic moiety, hetero-aromatic moiety, amino moiety, acyl moiety, ester moiety, amide moiety, cyano moiety, nitro group, aryl moiety.

In still another preferred example of this embodiment, an organometallic complex is represented by the following formula:

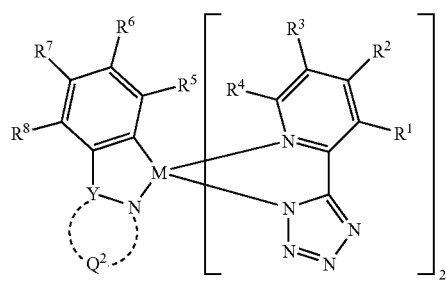

Concrete of the transition metal complex according to this embodiment will be illustrated bellow without intention of restricting the scope of the present invention defined by the claims attached hereto.

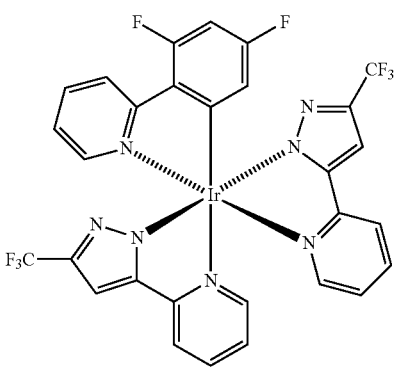

1a

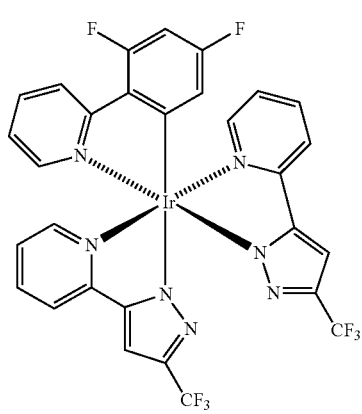

1b

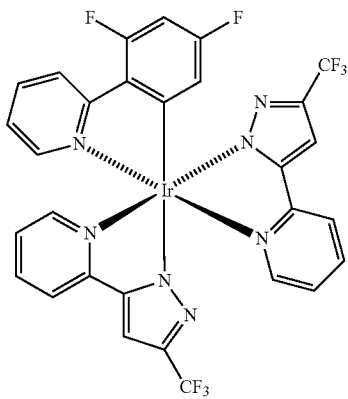

1c

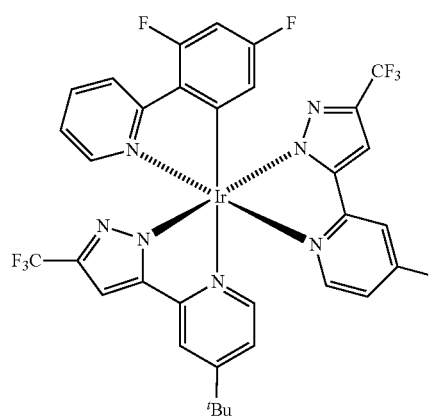

2a

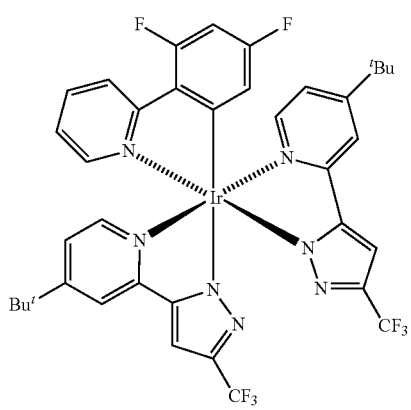

2b

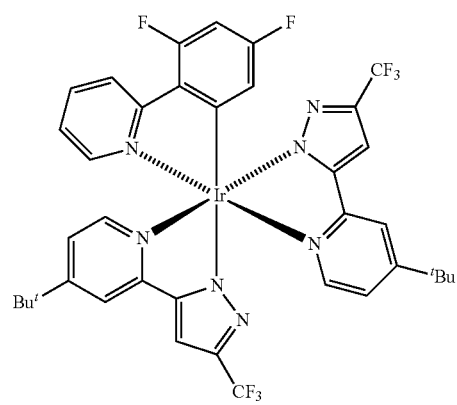

2c

-continued
3a
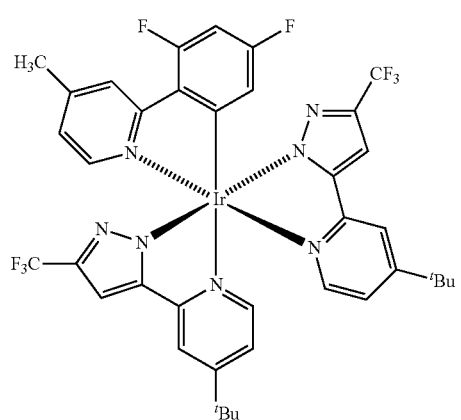
3b
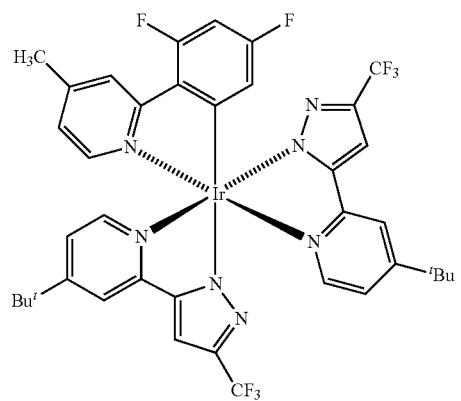
3c
4a
4b
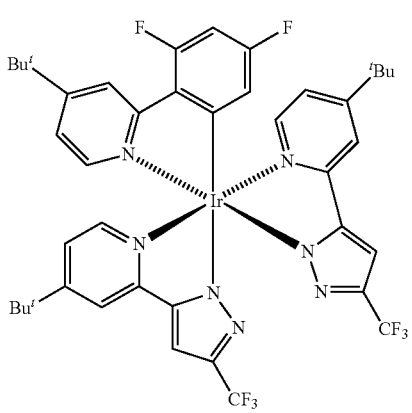
4c
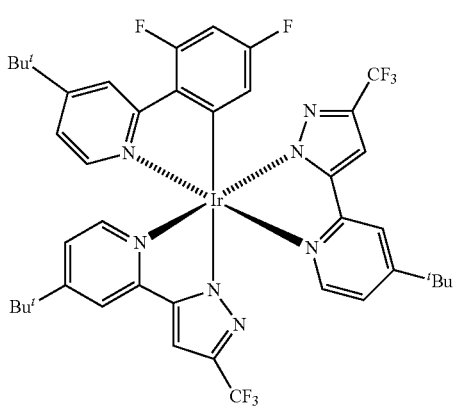
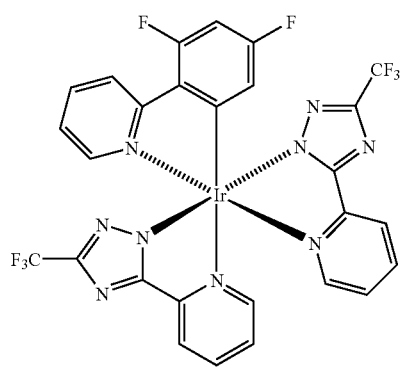
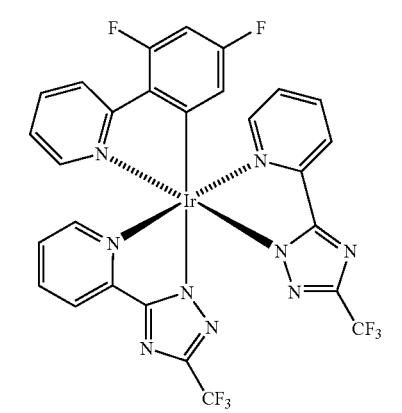

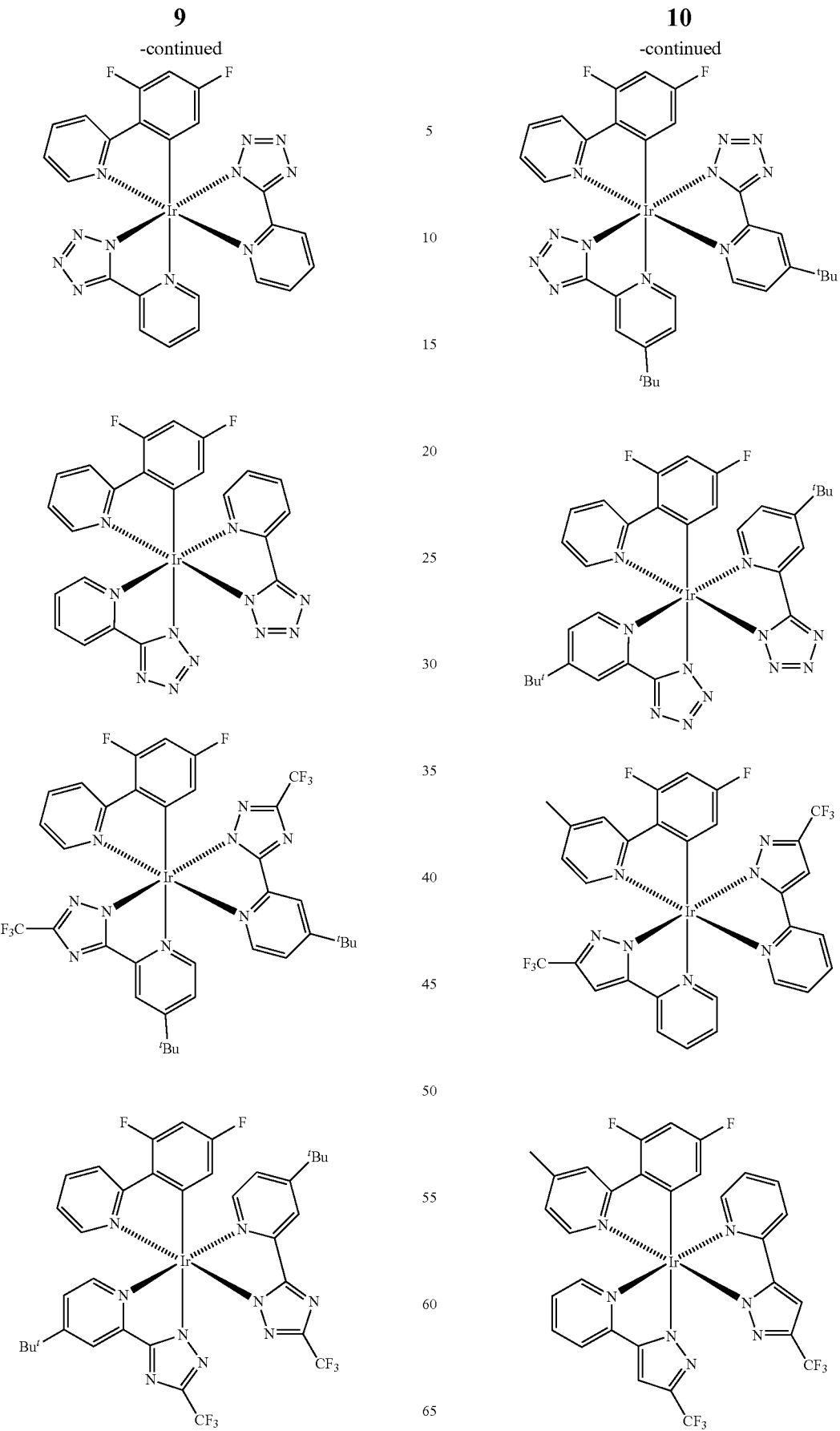

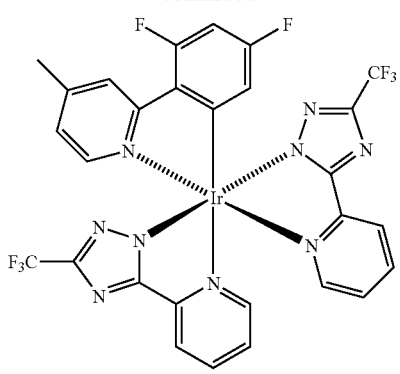
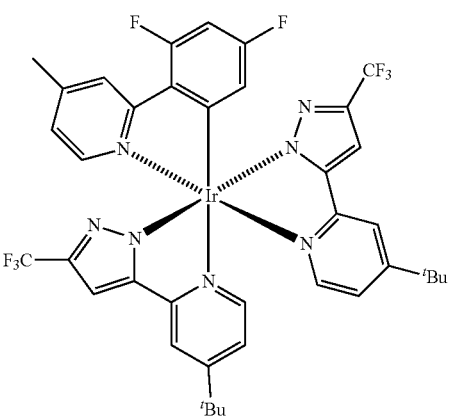
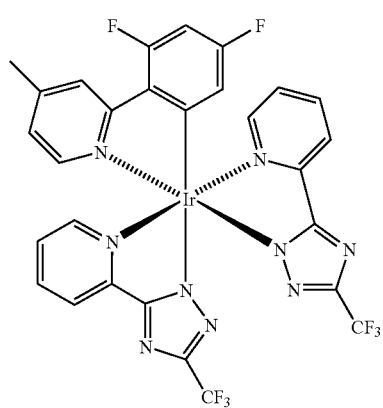
Concrete structure of the ligand,
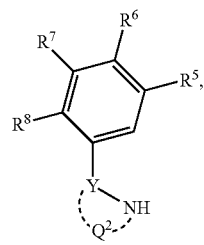
of the transition metal complex according to this embodiment will be illustrated bellow without intention of restricting the scope of the present invention defined by the claims attached hereto.
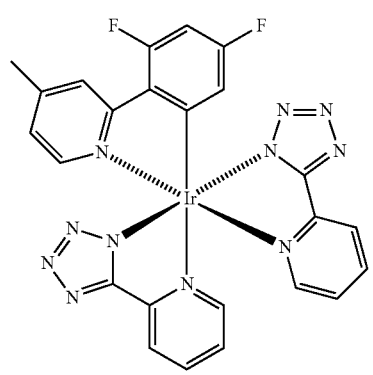
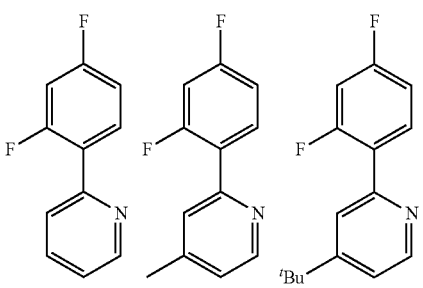
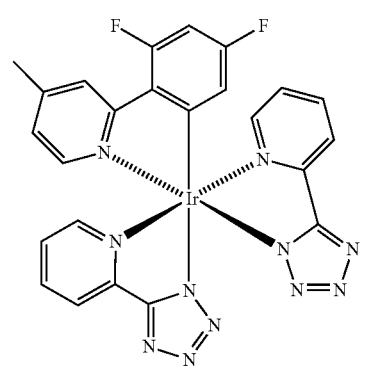
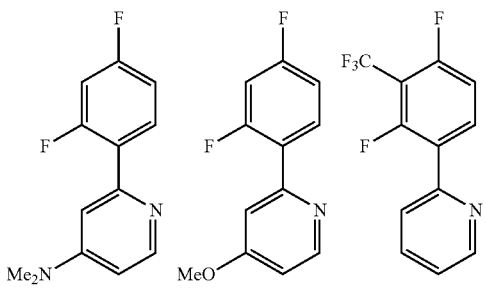

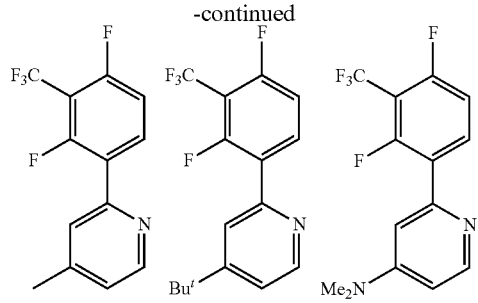
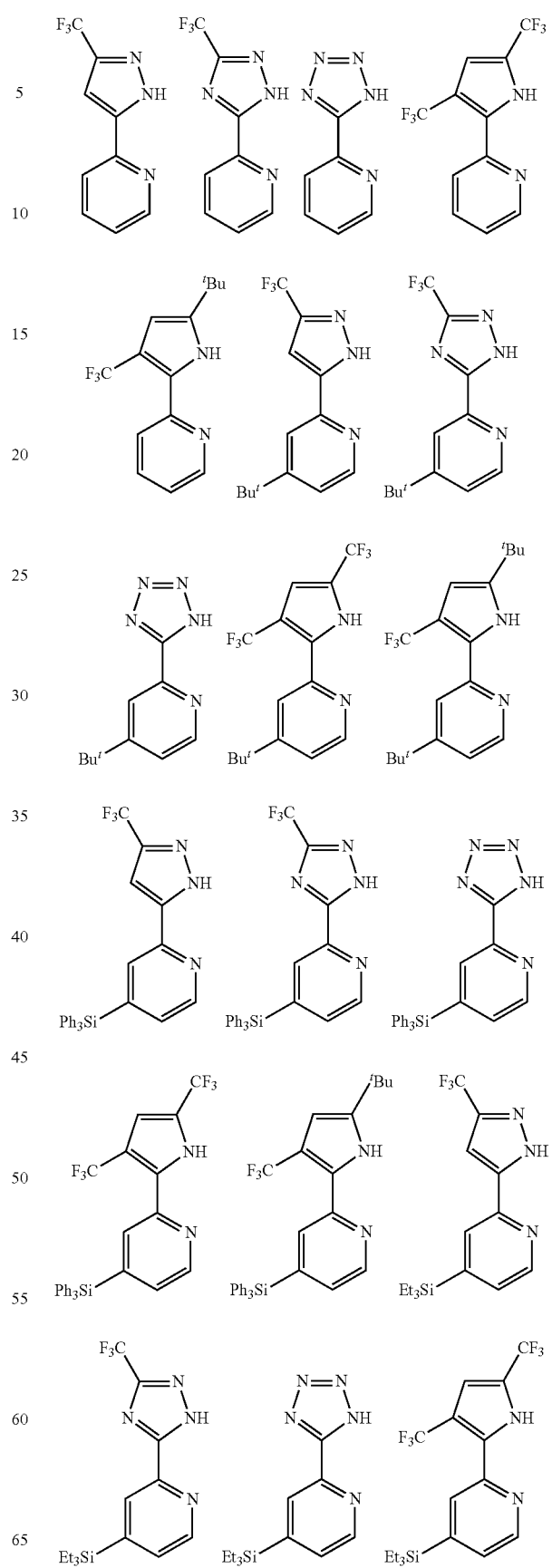
Concrete structure of the ligand,
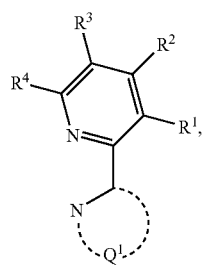
of the transition metal complex according to this embodiment will be illustrated bellow without intention of restricting the scope of the present invention defined by the claims attached hereto.

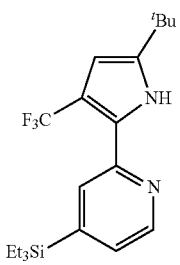

EXAMPLE 1

Ir(dfppy)(fppz)₂ [bis(3-(trifluoromethyl)-5-pyrazolato) iridium (III) 4',6'-difluorophenylpyridinate] 1a, 1b, and 1c

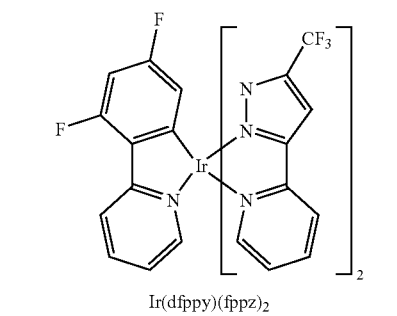

Ir(dfppy)(fppz)₂

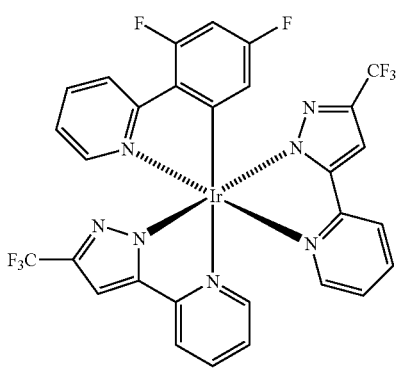

1a

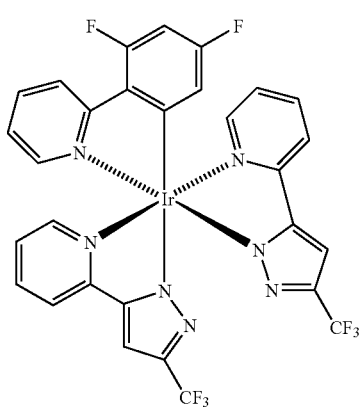

1b

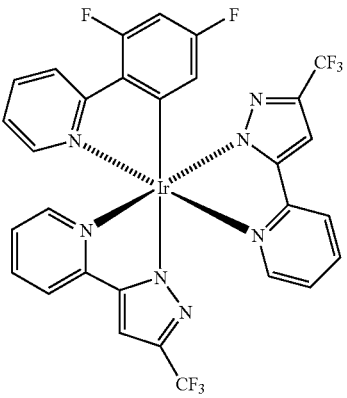

1c

Synthesis: A mixture of 4,6-difluorophenyl pyridine (0.20 g, 1.07 mmol) and $IrCl_3 \cdot 3H_2O$ (0.34 g, 0.97 mmol) in 2-methoxyethanol (20 mL) was refluxed for 4 hours under $N_2$. The mixture was then cooled to room temperature, and 0.43 g (2.04 mmol) fppzH and 0.45 g (4.27 mmol) $Na_2CO_3$ were added. The resulting mixture was refluxed for another 8 hours, and 20 mL deionized water was added after cooling the solution to RT. The yellow precipitate was collected by filtration. The precipitate was separated using silica gel column chromatography (ethyl acetate:hexane=1:1), giving a bright blue-emitting complex 1a (0.14 g, 0.17 mmol, 18%) together with complex 1b (0.13 g, 0.16 mmol, 16%) and 1c (0.14 g, 0.17 mmol, 18%) according to the sequence of their elution. The dicyclometalated complex [Ir(dfppy)₂(fppz)] (~12%) together with at least two unknown complexes were also detected in low yields. Single crystals of 1a and 1b were obtained from a mixture of $CH_2Cl_2$/methanol at room temperature.

Spectral data of 1a: MS (FAB, $^{192}$Ir): observed m/z [assignment]: 808 [M⁺+1]. $^1$H NMR (400 MHz, $d_6$-acetone, 294 K): δ 8.26 (d, $J_{HH}$=8.8 Hz, 1H), 8.18~8.03 (m, 4H), 7.94~7.90 (m, 2H), 7.44~7.39 (m, 3H), 7.32 (td, $J_{HH}$=5.6, 1.6 Hz, 1H), 7.23 (s, 1H), 7.21 (s, 1H), 7.16 (td, $J_{HH}$=6.2, 1.2 Hz, 1H), 6.63 (td, $J_{HH}$=8.2, 2.4 Hz, 1H), 5.82 (dd, $J_{HH}$=8.8, 2.4 Hz, 1H). $^{19}$F NMR (470 MHz, $d_6$-acetone, 294 K): δ −111.8 (s, 1F), −109.6 (s, 1F), −60.7 (s, 3F), −60.6 (s, 3F). Anal. Calcd. for $C_{29}H_{16}F_8IrN_7$: N, 12.15; C, 43.18; H, 2.00. Found: N, 12.03; C, 43.35; H, 2.02.

Spectral data of 1b: MS (FAB, $^{192}$Ir): observed m/z [assignment]: 808 [M⁺+1]. $^1$H NMR (400 MHz, $d_6$-acetone, 294 K): δ 8.38 (d, $J_{HH}$=8.8 Hz, 1H), 8.08~8.00 (m, 3H), 7.97~7.88 (m, 3H), 7.60 (dd, $J_{HH}$=12.4, 5.6 Hz, 2H), 7.36 (td, $J_{HH}$=6.0, 1.6 Hz, 1H), 7.21 (s, 1H), 7.19 (s, 1H), 7.15~7.10 (m, 2H), 6.74 (td, $J_{HH}$=9.6, 2.4 Hz, 1H), 5.82 (dd, $J_{HH}$=8.8, 2.4 Hz, 1H). $^{19}$F NMR (470 MHz, $d_6$-acetone, 294 K): δ −110.2 (s, 1F), −107.2 (s, 1F), −60.5 (s, 3F), −60.3 (s, 3F). Anal. Calcd. for $C_{29}H_{16}F_8IrN_7$: N, 12.15; C, 43.18; H, 2.00. Found: N, 12.11; C, 43.25; H, 2.02.

Spectral data of 1c: MS (FAB, $^{192}$Ir): observed m/z [assignment]: 808 [M⁺+1]. $^1$H NMR (500 MHz, $d_6$-acetone, 294 K): δ 8.32 (d, $J_{HH}$=8.5 Hz, 1H), 8.13~7.98 (m, 6H), 7.81 (d, $J_{HH}$=5.3 Hz, 1H), 7.68 (d, $J_{HH}$=6.5 Hz, 1H), 7.30 (td, $J_{HH}$=5.8, 1.0, 1H), 7.25~7.22 (m, 2H), 7.20 (s, 1H), 7.07 (s, 1H), 6.61 (td, $J_{HH}$=10, 2.5 Hz, 1H), 5.83 (dd, $J_{HH}$=8.5, 2.0 Hz, 1H). $^{19}$F NMR (470 MHz, $d_6$-acetone, 294 K): δ −111.9 (s, 1F), −108.8 (s, 1F), −60.5 (s, 3F), −60.4 (s, 3F). Anal. Calcd. for $C_{29}H_{16}F_8IrN_7$: N, 12.15; C, 43.18; H, 2.00. Found: N, 12.03; C, 43.12; H, 2.11.

EXAMPLE 2

Ir(dfppy)(fbppz)$_2$[bis(3-(trifluoromethyl)-5-(4-t-butylpyridyl)pyrazolato) iridium (III) 4',6'-difluorophenylpyridinate] 2a, 2b, and 2c

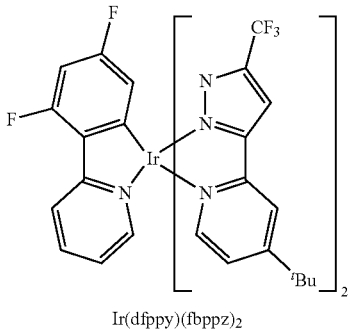

Ir(dfppy)(fbppz)$_2$

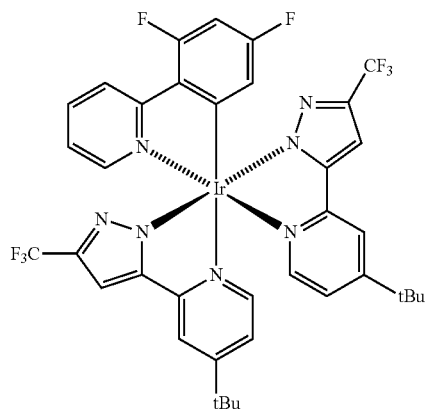

2a

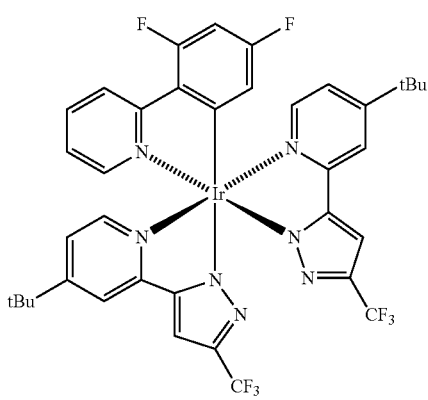

2b

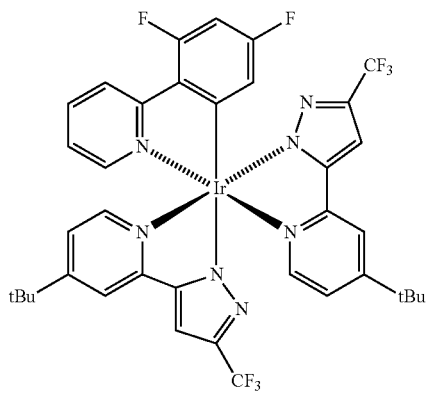

2c

Synthesis: A mixture of 4,6-difluorophenyl pyridine (0.24 g, 1.25 mmol) and IrCl$_3$.3H$_2$O (0.43 g, 1.23 mmol) in 2-methoxyethanol (20 mL) was refluxed for 4 hours under N$_2$. The mixture was then cooled to room temperature, and 0.69 g (2.56 mmol) 3-(trifluoromethyl)-5-(4-t-butylpyridyl)pyrazole and 1.3 g (12.2 mmol) Na$_2$CO$_3$ were added. The resulting mixture was refluxed for another 12 hours, and 20 mL deionized water was added after cooling the solution to RT. The yellow precipitate was collected by filtration. The precipitate was separated using silica gel column chromatography (ethyl acetate:hexane=1:2), giving a bright blue emissive complex 2a (0.22 g, 0.23 mmol, 20%) together with complex 2b (0.14 g, 0.15 mmol, 13%) and 2c (0.12 g, 0.14 mmol, 11%) according to the sequence of their elution. The dicyclometalated complex [Ir(dfppy)$_2$(fbppz)] (~13%) together with at least two unknown complexes were also detected in low yields.

Spectral data of 2a: MS (FAB, $^{192}$Ir): observed m/z [assignment]: 920 [M$^+$+1]. $^1$H NMR (500 MHz, d$_6$-acetone, 294 K): δ 8.25 (d, J$_{HH}$=8.0 Hz, 1H), 8.21 (d, J$_{HH}$=1.5 Hz, 1H), 8.18 (d, J$_{HH}$=2.0 Hz, 1H), 7.90 (t, J$_{HH}$=7.0 Hz, 1H), 7.84 (d, J$_{HH}$=6.0 Hz, 1H), 7.47 (dd, J$_{HH}$=5.0, 2.0 Hz, 1H), 7.38 (dd, J$_{HH}$=6.5, 2.5 Hz, 1H) 7.31~7.27 (m, 4H), 7.12 (t, J$_{HH}$=5.8 Hz, 1H), 6.62 (td, J$_{HH}$=9.5, 2.0 Hz, 1H), 5.82 (dd, J$_{HH}$=8.5, 2.0 Hz, 1H), 1.38 (s, 9H), 1.37 (s, 9H). $^{19}$F NMR (470 MHz, d$_6$-acetone, 294 K): δ −111.9 (s, 1F), −109.6 (s, 1F), −60.7 (s, 3F), −60.6 (s, 3F). Anal. Calcd. for $C_{37}H_{32}F_8IrN_7$: N, 10.67; C, 48.36; H, 3.51. Found: N, 10.41; C, 48.11; H, 2.25.Spectral data of 2b: MS (FAB, $^{192}$Ir): observed m/z [assignment]: 920 [M$^+$+1]. $^1$H NMR (500 MHz, d$_6$-acetone, 294 K): δ 8.37 (d, J$_{HH}$=8.0 Hz, 1H), 8.08~8.02 (m, 3H), 7.72 (d, J$_{HH}$=7.0 Hz, 1H), 7.59 (d, J$_{HH}$=6.0 Hz, 1H), 7.41 (d, J$_{HH}$=3.0 Hz, 1H), 7.36 (td, J$_{HH}$=9.8, 1.5 Hz, 1H), 7.30 (s, 1H), 7.27 (s, 1H), 7.16~7.13 (m, 2H), 6.74 (td, J$_{HH}$=10.0, 2.0 Hz, 1H), 5.84 (dd, J$_{HH}$=8.0, 2.5 Hz, 1H), 1.35 (s, 9H), 1.34 (s, 9H). $^{19}$F NMR (470 MHz, d$_6$-acetone, 294 K): δ −110.3 (s, 1F), −107.2 (s, 1F), −60.4 (s, 3F), −60.1 (s, 3F). Anal. Calcd. for $C_{37}H_{32}F_8IrN_7$: N, 10.67; C, 48.36; H, 3.51. Found: N, 10.52; C, 48.13; H, 3.12.

Spectral data of 2c: MS (FAB, $^{192}$Ir): observed m/z [assignment]: 920 [M$^+$+1]. $^1$H NMR (500 MHz, d$_6$-acetone, 294 K): δ 8.26 (d, J$_{HH}$=8.0 Hz, 1H), 8.17 (d, J$_{HH}$=2.0 Hz, 1H), 8.12 (d, J$_{HH}$=2.5 Hz, 1H), 7.93 (t, J$_{HH}$=8.0 Hz, 1H), 7.74~7.72 (m, 2H), 7.49 (d, J$_{HH}$=6.0 Hz, 1H), 7.35 (s, 1H), 7.27 (dd, J$_{HH}$=6.0, 2.0 Hz, 1H), 7.24~7.19 (m, 2H), 7.16 (s, 1H), 6.72 (td, J$_{HH}$=9.7, 2.0 Hz, 1H), 5.97 (dd, J$_{HH}$=8.5, 3.0 Hz, 1H), 1.38 (s, 9H), 1.35 (s, 9H). $^{19}$F NMR (470 MHz, 294 K): δ −110.5 (s, 1F), −108.3 (s, 1F), −60.4 (s, 3F), −60.3

(s, 3F). Anal. Calcd. for $C_{37}H_{32}F_8IrN_7$: N, 10.67; C, 48.36; H, 3.51. Found: N, 10.66; C, 48.51; H, 3.10.

EXAMPLE 3

Ir(dfmppy)(fbppz)$_2$[bis(3-(trifluoromethyl)-5-(4-t-butylpyridyl)pyrazolato) iridium (III) 2-(2,4-difluorophenyl)-4-methylpyridinate] 3a, 3b, and 3c

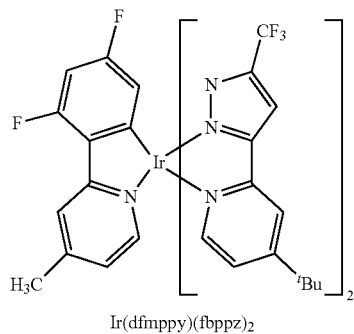

Ir(dfmppy)(fbppz)$_2$

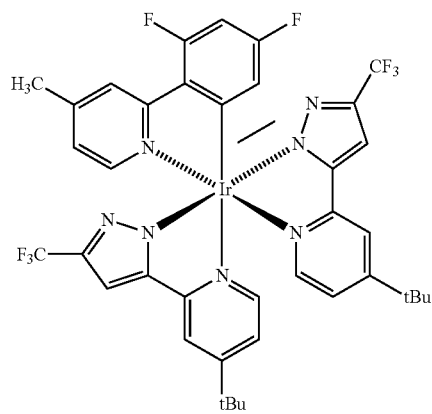

3a

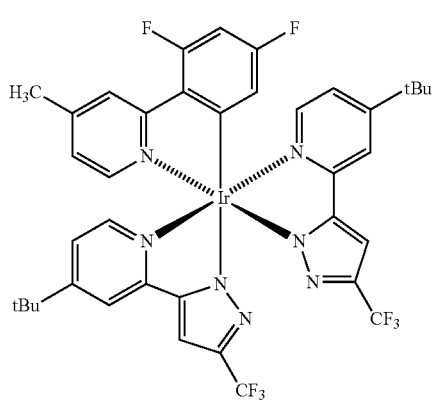

3b

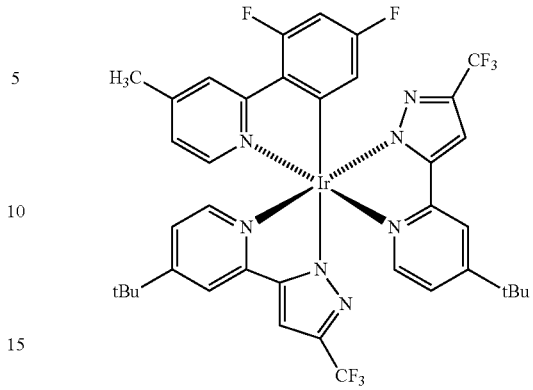

3c

Synthesis: A mixture of 2-(2,4-difluorophenyl)-4-methylpyridine (0.20 g, 0.97 mmol) and IrCl$_3$.3H$_2$O (0.34 g, 0.97 mmol) in 2-methoxyethanol (20 mL) was refluxed for 4 hours under N$_2$. The mixture was then cooled to room temperature, and 0.54 g (2.01 mmol) 3-(trifluoromethyl)-5-(4-t-butylpyridyl)pyrazole and 0.51 g (4.81 mmol) Na$_2$CO$_3$ were added. The resulting mixture was refluxed for another 12 hours, and 20 mL deionized water was added after cooling the solution to RT. The yellow precipitate was collected by filtration. The precipitate was separated using silica gel column chromatography (ethyl acetate:hexane=1:2), giving a bright blue-emitting complex 3a (0.17 g, 0.18 mmol, 19%) together with a second complex 3b (0.11 g, 0.11 mmol, 12%) and 3c (0.11 g, 0.12 mmol, 11%) according to the sequence of their elution. The dicyclometalated complex [Ir(dfmppy)$_2$(fbppz)] (~13%) together with at least two unknown complexes were also detected in low yields.

Spectral data of 3a: MS (FAB, $^{192}$Ir): observed m/z [assignment]: 934 [M$^+$+1]. $^1$H NMR (500 MHz, d$_6$-acetone, 294 K): δ 8.18 (dd, J$_{HH}$=15.0, 2.0 Hz, 2H), 8.06 (s, 1H), 7.63 (d, J$_{HH}$=6.0 Hz, 1H), 7.46 (dd, J$_{HH}$=6.5, 2.5 Hz, 1H), 7.37 (dd, J$_{HH}$=6.5, 2.5 Hz, 1H), 7.30~7.27 (m, 4H), 6.95 (d, J$_{HH}$=5.5 Hz, 1H), 6.60 (t, J$_{HH}$=11.5 Hz, 1H), 5.80 (dd, J$_{HH}$=8.0, 2.0 Hz, 1H), 2.53 (s, 3H), 1.38 (s, 9H), 1.37 (s, 9H). $^{19}$F NMR (470 MHz, d$_6$-acetone, 294 K): δ −111.8 (s, 1F), −109.9 (s, 1F), −60.6 (s, 3F), −60.5 (s, 3F). Anal. Calcd. for $C_{38}H_{34}F_8IrN_7$: N, 10.51; C, 48.92; H, 3.67. Found: N, 10.56; C, 49.01; H, 3.52.

Spectral data of 3b: MS (FAB, $^{192}$Ir): observed m/z [assignment]: 934 [M$^+$+1]. $^1$H NMR (500 MHz, d$_6$-acetone, 294 K): δ 8.19 (s, 1H), 8.06 (dd, J$_{HH}$=8.0, 2.0 Hz, 1H), 7.71 (d, J$_{HH}$=6.0 Hz, 1H), 7.40 (t, J$_{HH}$=6.5 Hz, 1H), 7.29 (s, 1H), 7.26 (s, 1H), 7.21 (dd, J$_{HH}$=6.0, 1.0 Hz, 1H), 7.15~7.13 (m, 2H), 6.72 (td, J$_{HH}$=9.3, 3.0 Hz, 1H), 5.83 (dd, J$_{HH}$=8.0, 2.0 Hz, 1H), 2.58 (s, 3H), 1.34 (s, 9H), 1.24 (s, 9H). $^{19}$F NMR (470 MHz, d$_6$-acetone, 294 K): δ −110.2 (s, 1F), −107.6 (s, 1F), −60.4 (s, 3F), −60.1 (s, 3F). Anal. Calcd. for $C_{38}H_{34}F_8IrN_7$: N, 10.51; C, 48.92; H, 3.67. Found: N, 10.44; C, 48.86; H, 3.41.

Spectral data of 3c: MS (FAB, $^{192}$Ir): observed m/z [assignment]: 934 [M$^+$+1]. $^1$H NMR (500 MHz, d$_6$-acetone, 294 K): δ 8.26 (d, J$_{HH}$=8.0 Hz, 1H), 8.17 (d, J$_{HH}$=2.0 Hz, 1H), 8.12 (d, J$_{HH}$=2.5 Hz, 1H), 7.93 (t, J$_{HH}$=8.0 Hz, 1H), 7.74~7.72 (m, 2H), 7.49 (d, J$_{HH}$=6.0 Hz, 1H), 7.35 (s, 1H), 7.27 (dd, J$_{HH}$=6.0, 2.0 Hz, 1H), 7.24~7.19 (m, 2H), 7.16 (s, 1H), 6.72 (td, J$_{HH}$=9.7, 2.0 Hz, 1H), 5.97 (dd, J$_{HH}$=8.5, 3.0 Hz, 1H), 2.52 (s, 9H), 1.38 (s, 9H), 1.35 (s, 9H). $^{19}$F NMR (470 MHz, d$_6$-acetone, 294 K): δ −110.5 (s, 1F), −108.3 (s, 1F), −60.4 (s, 3F), −60.3 (s, 3F). Anal. Calcd. for $C_{38}H_{34}F_8IrN_7$: N, 10.51; C, 48.92; H, 3.67. Found: N, 10.62; C, 49.10; H, 3.24.

EXAMPLE 4

Ir(dfbppy)(fbppz)₂[bis(3-(trifluoromethyl)-5-(4-t-butylpyridyl)pyrazolato) iridium (III) 4-tert-butyl-2-(2,4-difluorophenyl)pyridinate] 4a, 4b, and 4c

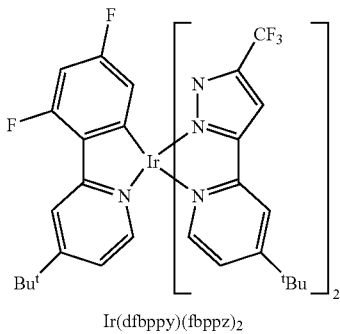

Ir(dfbppy)(fbppz)₂

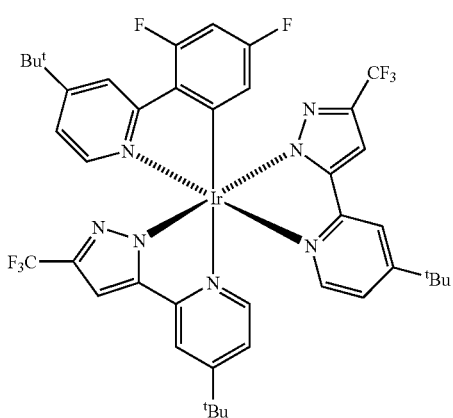

4a

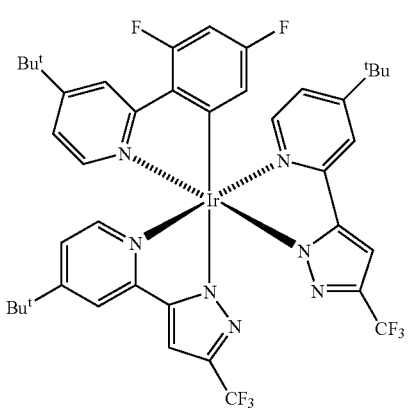

4b

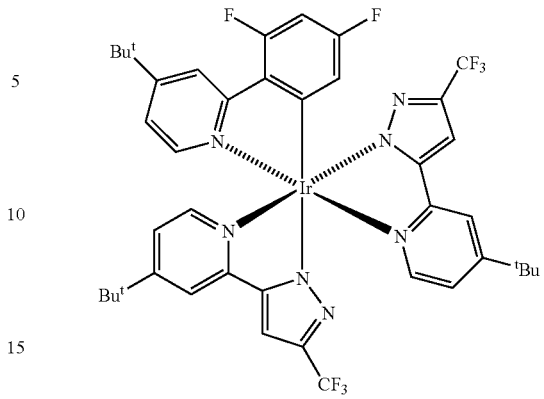

4c

Synthesis: A mixture of 4-tert-butyl-2-(2,4-difluorophenyl)pyridine (0.38 g, 1.53 mmol) and $IrCl_3 \cdot 3H_2O$ (0.48 g, 1.37 mmol) in 2-methoxyethanol (20 mL) was refluxed for 4 hours under $N_2$. The mixture was then cooled to room temperature, and 0.78 g (2.90 mmol) 3-(trifluoromethyl)-5-(4-t-butylpyridyl)pyrazole and 0.95 g (8.97 mmol) $Na_2CO_3$ were added. The resulting mixture was refluxed for another 12 hours, and 20 mL deionized water was added after cooling the solution to RT. The yellow precipitate was collected by filtration. The precipitate was separated using silica gel column chromatography (ethyl acetate: hexane=1:2), giving a bright blue-emitting complex 4a (0.20 g, 0.21 mmol, 17%) together with a second complex 4b (0.19 g, 0.19 mmol, 16%) and complex 4c (0.14 g, 0.15 mmol, 12%) according to the sequence of their elution. The dicyclometalated complex [Ir(dfbppy)₂(fbppz)] (~11%) together with at least two unknown complexes were also detected in low yields.

Spectral data of 4a: MS (FAB, $^{192}$Ir): observed m/z [assignment]: 976 [M⁺+1]. ¹H NMR (400 MHz, CDCl₃, 294 K): δ 8.23 (t, $J_{HH}$=2.4 Hz, 1H), 7.67 (d, $J_{HH}$=2.0 Hz, 1H), 7.62 (d, $J_{HH}$=2.4 Hz, 1H), 7.38 (d, $J_{HH}$=2.0 Hz, 1H), 7.22~7.20 (m, 2H), 7.15 (dd, $J_{HH}$=6.0, 1.6 Hz, 1H), 7.04 (dd, $J_{HH}$=5.2, 2.0 Hz, 1H), 6.91 (s, 1H), 6.90~7.89 (m, 2H), 6.46 (dt, $J_{HH}$=9.6, 2.0 Hz, 1H), 5.72 (dd, $J_{HH}$=8.8, 1.6 Hz, 1H), 1.34 (s, 9H), 1.33 (s, 9H), 1.32 (s, 9H). ¹⁹F NMR (470 MHz, CDCl₃, 294 K): δ −110.5 (s, 1F), −108.5 (s, 1F), −60.1 (s, 6F) Anal. Calcd. for $C_{41}H_{40}F_8IrN_7$: N, 10.06; C, 50.51; H, 4.14. Found: N, 10.12; C, 50.66; H, 4.28.

Spectral data of 4b: MS (FAB, $^{192}$Ir): observed m/z [assignment]: 976 [M⁺+1]. ¹H NMR (400 MHz, CDCl₃, 294 K): δ 8.26 (t, $J_{HH}$=3.0 Hz, 1H), 7.67 (d, $J_{HH}$=6.5 Hz, 1H), 7.59 (d, $J_{HH}$=11.5 Hz, 1H), 7.36 (d, $J_{HH}$=6.5 Hz, 1H), 7.13 (d, $J_{HH}$=7.0 Hz, 1H), 7.06 (dd, $J_{HH}$=6.0, 2.0 Hz, 1H), 6.96 (s, 1H), 6.91 (s, 1H), 6.92~6.90 (m, 2H), 6.85 (td, $J_{HH}$=6.0, 2.0 Hz, 1H), 6.50 (td, $J_{HH}$=9.8, 2.5 Hz, 1H), 5.85 (dd, $J_{HH}$=6.0, 2.0 Hz, 1H), 1.34 (s, 9H), 1.30 (s, 9H), 1.29 (s, 9H). ¹⁹F NMR (470 MHz, CDCl₃, 294 K): δ −109.9 (s, 1F), −105.2 (s, 1F), −60.1 (s, 3F), −59.8 (s, 3F). Anal. Calcd. for $C_{41}H_{40}F_8IrN_7$: N, 10.06; C, 50.51; H, 4.14. Found: N, 10.12; C, 50.66; H, 4.28.

Spectral data of 4c: MS (FAB, $^{192}$Ir): observed m/z [assignment]: 976 [M⁺+1]. ¹H NMR (500 MHz, CDCl₃, 294 K): δ 8.18 (t, $J_{HH}$=2.0 Hz, 1H), 7.66 (dd, $J_{HH}$=5.5, 2.5 Hz, 2H), 7.60 (d, $J_{HH}$=6.0 Hz, 1H), 7.56 (d, $J_{HH}$=13.0 Hz, 1H), 7.13 (d, $J_{HH}$=6.0, 1H), 7.02 (dd, $J_{HH}$=6.5, 2.0 Hz, 2H), 6.97 (s, 1H), 6.98~6.94 (m, 2H), 6.89 (s, 1H), 6.51 (td, $J_{HH}$=9.8, 2.0 Hz, 1H), 5.83 (dd, $J_{HH}$=7.5, 2.0 Hz, 1H), 1.33 (s, 9H), 1.32 (s, 9H), 1.31 (s, 9H). ¹⁹F NMR (470 MHz, CDCl₃, 294 K): δ −109.5 (s, 1F), −107.6 (s, 1F), −60.2 (s, 3F), −60.0 (s, 3F).

Anal. Calcd. for $C_{41}H_{40}F_8IrN_7$: N, 10.06; C, 50.51; H, 4.14. Found: N, 10.12; C, 50.66; H, 4.28.

The photophysical data of iridium(III) complexes 1a to 4c is shown as the following Table 1:

TABLE 1

| | em. $\lambda_{max}$/nm[a] | Q. Y. | $\tau_{obs}$/μs | $\tau_r$/μs |
|---|---|---|---|---|
| 1a | 450, 479, 511 (sh), 554 (sh) | 0.50[a]<br>0.45[c] | 3.8[a]<br>6.7[b] | 7.7[a] |
| 1b | 450, 480, 515 (sh), 545 (sh) | 0.14[a]<br>0.28[c] | 4.4[a]<br>8.2[b] | 31.1[a] |
| 1c | 454, 482, 515(sh), 560(sh) | 0.34[a] | 2.3[a] | 6.6[a] |
| 2a | 451, 480, 511 (sh), 546 (sh) | 0.83[a]<br>0.74[c] | 3.9[a] | 4.7[a] |
| 2b | 453, 481, 507 (sh), 548 (sh) | 0.10[a] | 3.8[a] | 38[a] |
| 2c | 452, 482, 507 (sh), 544 (sh) | 0.36[a] | 4.3[a] | 11.9[a] |
| 3a | 447, 475, 502 (sh), 546 (sh) | 0.58[a] | 3.2[a] | 5.5[a] |
| 3b | 445, 476, 505 (sh), 545 (sh) | 0.01[a] | 2.0[a] | 222[a] |
| 3c | 448, 477, 506 (sh), 549 (sh) | 0.18[a] | 3.5[a] | 19.4[a] |
| 4a | 449, 479, 507 (sh), 546 (sh) | 0.47[a] | 2.8[a] | 5.5[a] |
| 4b | 456, 481, 511 (sh), 545 (sh) | 0.01[a] | 2.7[a] | 270[a] |
| 4c | 448, 477, 507 (sh), 543 (sh) | 0.25[a] | 3.0[a] | 12.0[a] |

[a]data obtained in degassed $CH_2Cl_2$;
[b]obtained at 77 K in $CH_2Cl_2$ matrix;
[c]Obtained from samples in a doped thin film by using CzSi as the host material.

Despite their structural isomerism, salient differences in photophysical behaviors are observed. In degassed $CH_2Cl_2$, complex 1a displays highly efficient, blue phosphorescence ($\lambda_{max}$~450 nm, Q.Y. ~0.50) at room temperature; isomer 1b is inferior by ~3.5 folds in phosphorescence efficiency. While the nonradiative decay rate is more or less the same, the difference in Q.Y. is apparently attributed to a shorter radiative lifetime in 1a. The results, in combination with computational approaches (DFT), lead the present invention to propose a structurally imposed luminescent behavior, confirming that the MLCT (metal-to-ligand charge transfer) contribution in the lowest energy excited state is a critical factor in enhancing the room temperature phosphorescence. Complex 1a also exhibits a high Q.Y. of 0.40 in the solid film. As a result, fabrication of complex 1a successfully achieves true-blue OLEDs, showing a bright blue emission with $\lambda_{max}$ ~450 nm, luminance efficiency 7.69 cd/A and an external quantum efficiency of 5.02% with CIE of (0.166, 0.213).

The second embodiment of the present invention discloses an light emitting device comprising a pair of electrodes and one or more organic layers disposed between said electrodes, said one or more organic layers comprising a light-emitting layer, wherein at least one of said one or more organic layer comprises an organometallic complex represented by the following formula:

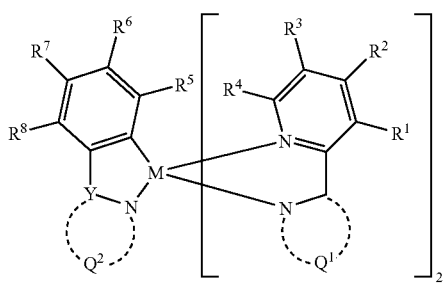

Complex A

In the mentioned structure, M represents a transition metal selected from the group consisting of ruthenium, rhodium, tungsten, rhenium, osmium, iridium, and platinum. Y is selected from the group consisted of C, and N. $Q^1$ and $Q^2$ respectively represent an atomic group forming a nitrogen-containing heterocyclic ring. The atoms of the atomic group of $Q^1$ and $Q^2$ are respectively selected from the group consisted of: C, N, P, O, and S. According to this embodiment, the nitrogen-containing heterocyclic ring formed with $Q^1$ and $Q^2$ are selected from the group consisted of: a five member ring, a six member ring, a seven member ring, respectively.

In one preferred example of this embodiment, the mentioned nitrogen-containing heterocyclic ring formed with $Q^1$ and $Q^2$ can further comprise at least one substituent, and the substituent is selected from the group consisted of: hydrogen atom, halide atom, alkyl moiety, alkenyl moiety, halo-alkyl moiety, alkoxyl moiety, aromatic moiety, hetero-aromatic moiety, amino moiety, acyl moiety, ester moiety, amide moiety, cyano moiety, nitro group, aryl moiety.

According to this embodiment, $R^1$, $R^2$, $R^3$, $R^4$, $R^5$, $R^6$, $R^7$, and $R^8$ in the above structure can be identical or different, and $R^1$, $R^2$, $R^3$, $R^4$, $R^5$, $R^6$, $R^7$, and $R^8$ are respectively selected from the group consisting of a hydrogen atom, halide atom, alkyl moiety, alkenyl moiety, halo-alkyl moiety, alkoxyl moiety, aromatic moiety, hetero-aromatic moiety, amino moiety, acyl moiety, ester moiety, amide moiety, cyano moiety, nitro group, aryl moiety, tri-alkylsilyl moiety, tri-aryl silyl moiety.

One preferred example of this embodiment discloses an organometallic complex represented by the following formula:

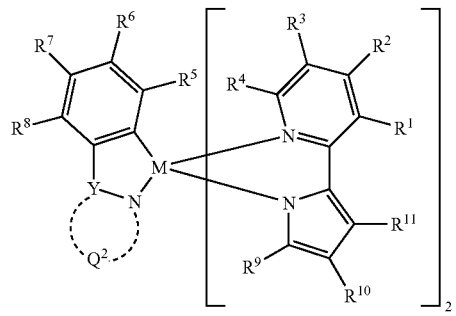

In the above structure, $R^9$, $R^{10}$, and $R^1$ are identical or different, and $R^9$, $R^{10}$, and $R^{11}$ are respectively selected from the group consisting of a hydrogen atom, halide atom, alkyl moiety, alkenyl moiety, halo-alkyl moiety, alkoxyl moiety, aromatic moiety, hetero-aromatic moiety, amino moiety, acyl moiety, ester moiety, amide moiety, cyano moiety, nitro group, aryl moiety.

In another preferred example of this embodiment, an organometallic complex is disclosed as the following formula:

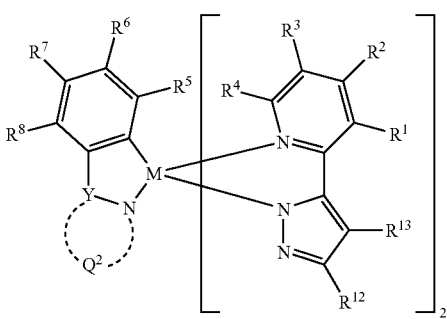

In the above structure, $R^{12}$, and $R^{13}$ are identical or different, and $R^{12}$, and $R^{13}$ are respectively selected from the group consisting of a hydrogen atom, halide atom, alkyl moiety, alkenyl moiety, halo-alkyl moiety, alkoxyl moiety, aromatic moiety, hetero-aromatic moiety, amino moiety, acyl moiety, ester moiety, amide moiety, cyano moiety, nitro group, aryl moiety.

In still another preferred example of this embodiment, an organometallic complex is represented by the following formula:

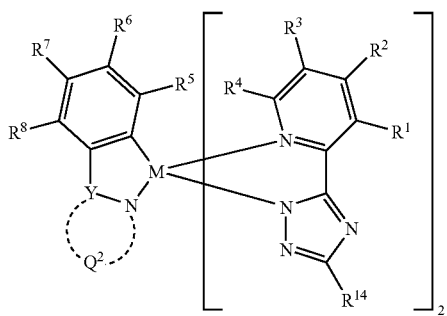

In the above structure, $R^{14}$ is selected from the group consisting of a hydrogen atom, halide atom, alkyl moiety, alkenyl moiety, halo-alkyl moiety, alkoxyl moiety, aromatic moiety, hetero-aromatic moiety, amino moiety, acyl moiety, ester moiety, amide moiety, cyano moiety, nitro group, aryl moiety.

In still another preferred example of this embodiment, an organometallic complex is represented by the following formula:

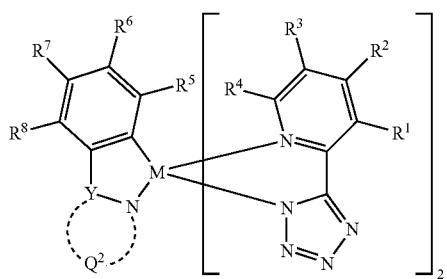

General Method of Producing OLEDs

Synthesized compounds according to this disclosed specification were subject to purification by temperature-gradient sublimation in high vacuum before use in subsequent device studies. OLEDs were fabricated on the ITO-coated glass substrates with multiple organic layers sandwiched between the transparent bottom indium-tin-oxide (ITO) anode and the top metal cathode. The material layers were deposited by vacuum evaporation in a vacuum chamber with a base pressure of $<10^{-6}$ torr. The deposition system permits the fabrication of the complete device structure in a single vacuum pump-down without breaking vacuum. The deposition rate of organic layers was kept at ~0.2 nm/s. The active area of the device is $2\times2$ mm$^2$, as defined by the shadow mask for cathode deposition.

Figure 4:
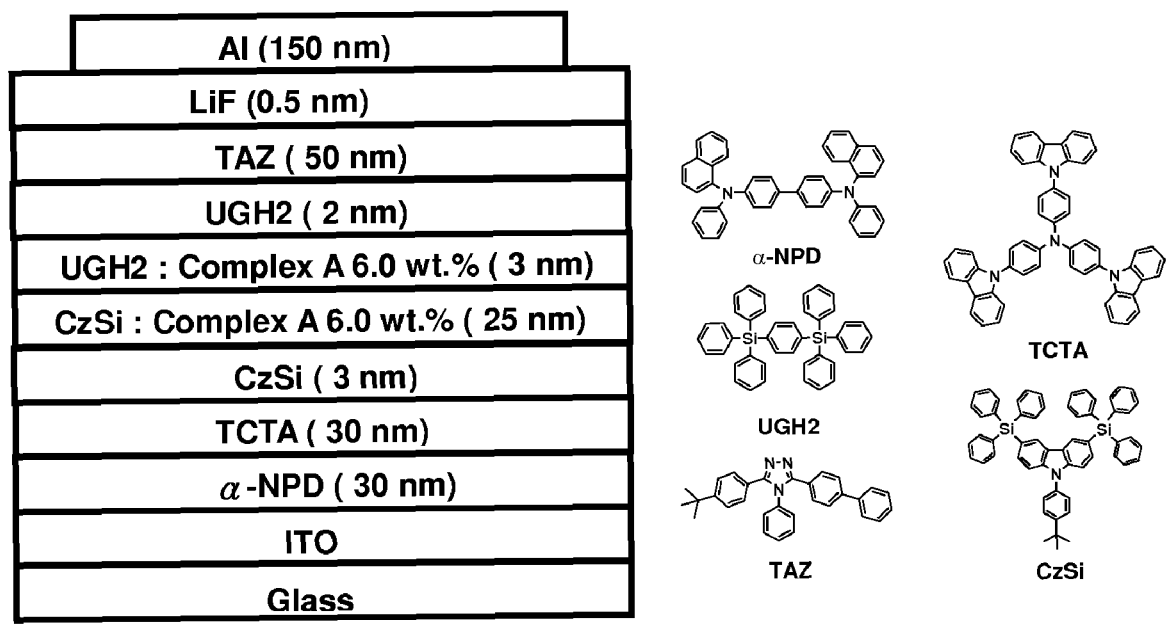
FIG. 4 shows one device structure and the materials used thereof according to one embodiment of this specification.

A device structure and materials used, as shown in FIG. 4, were ITO/α-NPD (~300 Å)/TCTA (300 Å)/CzSi (30 Å)/CzSi doped with ~6.0 wt. % of complex A (250 Å)/UGH2 doped with 6.0 wt. % of complex A (30 Å)/UGH2 (20 Å)/TAZ (500 Å)/LiF (5 Å)/Al (1500 Å). The α-naphthylphenylbiphenyl diamine (α-NPD) and 4,4',4"-tri(N-carbazolyl)triphenylamine (TCTA) were used as the hole-transport layer (HTL). The thin CzSi (30 Å) was served both as the hole-transport layer and as the buffer layer for blocking the high-energy triplet excitons (on complex A) from migrating to TCTA (with a lower triplet energy). Double emitting layers (CzSi and UGH2 doped with 6.0 wt. % of complex A) were used to achieve better balance between hole and electron injection/transport and thus to move the exciton formation zone away from the quenching interfaces with carrier-transport layers, taking advantage of the hole-transport nature of CzSi and the electron-transport nature of UGH2. The thin UGH2 (20 Å) was served both as the electron-transport/hole-blocking layer and as the buffer layer for blocking the high-energy triplet excitons from migrating to TAZ (with a lower triplet energy). Finally, 3-(4-biphenylyl)-4-phenyl-5-(4-tert-butylphenyl)-1,2,4-triazole (TAZ) was used as the electron-transport layer, and LiF or $Cs_2CO_3$ were used as the electron-injection layer.

The current-voltage-brightness (I-V-L) characterization of the light-emitting devices was performed with a source-measurement unit (SMU) and a calibrated Si photodiode with Photo Research PR650. EL spectra of devices were collected by a calibrated CCD spectrograph.

EXAMPLE 5

Using a procedure analogous to the abovementioned general method, blue-emitting OLEDs having the following structure were produced.

Device 1:
ITO/α-NPD (300 Å)/TCTA (300 Å)/CzSi (30 Å)/CzSi doped with 6.0 wt. % of complex 1a (250 Å)/UGH2 doped with 6.0 wt. % of complex 1a (30 Å)/UGH2 (20 Å)/TAZ (500 Å)/LiF (5 Å)/Al (1500 Å)

Device 2:
ITO/α-NPD (300 Å)/TCTA (300 Å)/CzSi (30 Å)/CzSi doped with 6.0 wt. % of complex 2a (250 Å)/UGH2 doped with 6.0 wt. % of complex 2a (30 Å)/UGH2 (20 Å)/TAZ (500 Å)/LiF (5 Å)/Al (1500 Å)

Device 3:
ITO/α-NPD (300 Å)/TCTA (300 Å)/CzSi (30 Å)/CzSi doped with 6.0 wt. % of complex 3a (250 Å)/UGH2 doped with 6.0 wt. % of complex 3a (30 Å)/UGH2 (20 Å)/TAZ (500 Å)/LiF (5 Å)/Al (1500 Å)

Device 4:
ITO/α-NPD (300 Å)/TCTA (300 Å)/CzSi (30 Å)/CzSi doped with 6.0 wt. % of complex 4a (250 Å)/UGH2 doped with 6.0 wt. % of complex 4a (30 Å)/UGH2 (20 Å)/TAZ (500 Å)/LiF (5 Å)/Al (1500 Å)

The photophysical data of the mentioned devices are shown as Table 2.

TABLE 2

| Device | | External Quantum Efficiency (%) | Luminance Efficiency (cd/A) | Power Efficiency (lm/W) | CIE coordinate (x, y) (@ 1000 cd/m2) |
|---|---|---|---|---|---|
| 1 | LiF | Peak | 8.6 | 13.1 | 8.2 | (0.159, 0.203) |
| | | 100 cd/m² | 7.1 | 10.8 | 4.3 | |
| 2 | LiF | Peak | 11.0 | 18.0 | 12.8 | (0.159, 0.224) |
| | | 100 cd/m² | 9.3 | 15.1 | 7.0 | |
| 3 | LiF | Peak | 13.0 | 20.0 | 14.1 | (0.158, 0.202) |
| | | 100 cd/m² | 10.1 | 15.5 | 6.6 | |
| 4 | LiF | Peak | 13.7 | 20.4 | 14.0 | (0.157, 0.189) |
| | | 100 cd/m² | 11.5 | 16.7 | 7.5 | |

All devices exhibit turn-on voltage slightly lower than 4V. Although the energy-gap of complexes is different, the maximum external quantum efficiencies of devices are achieving the theoretical limitation. As the carrier balance and exciton confinement being improved simultaneously, this architecture is potentially suitable for fabrocation of true blue devices using Ir complexes. According to the plots of efficiency data, all devices have approaching the carrier balance condition at low current density. Although the efficiency roll-off at higher current density typical in phosphorescent OLEDs is also observed here, the devices retain their high efficiency at the practical brightness of 100 cd/m². This decline in efficiency at the higher current is probable due to triplet-triplet annihilation. Compare with the efficiency of all devices, Device 4 has the highest efficiency of 13.7% (20.4 cd/A, 14 lm/W and the maximum brightness goes up to about 14,500 cd/m² at 18 V. The EL spectra of all devices exhibit true blue emission and the CIE y value near 0.2. Particularly, Device 4 shows the most saturated blue emission with CIE coordinates of (0.157, 0.189).

Obviously many modifications and variations are possible in light of the above teachings. It is therefore to be understood that within the scope of the appended claims the present invention can be practiced in various different examples and are not intended to limit to those specifically described herein. Although specific embodiments have been illustrated and described herein, it is obvious to those skilled in the art that many modifications of the present invention may be made without departing from what is intended to be limited solely by the appended claims.

What is claimed is:

1. An organometallic complex represented by the following formula:

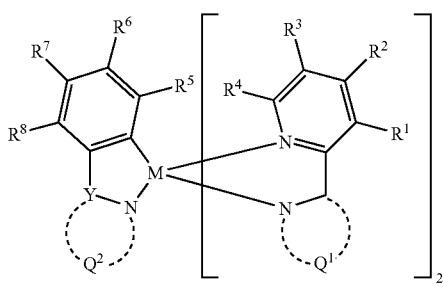

wherein M represents a transition metal selected from the group consisting of ruthenium, rhodium, tungsten, rhenium, osmium, iridium, and platinum; $Q^1$ and $Q^2$ respectively represent an atomic group forming a nitrogen-containing heterocyclic ring, wherein $Q^1$ is selected from the group consisted of: a five member ring, a seven member ring, wherein $Q^2$ is selected from the group consisted of: a five member ring, a six member ring, a seven member ring; Y is selected from the group consisted of C, and N; $R^1$, $R^2$, $R^3$, $R^4$, $R^5$, $R^6$, $R^7$, and $R^8$ are identical or different, and $R^1$, $R^2$, $R^3$, $R^4$, $R^5$, $R^6$, $R^7$, and $R^8$ are respectively selected from the group consisting of a hydrogen atom, halide atom, alkyl moiety, alkenyl moiety, halo-alkyl moiety, alkoxyl moiety, aromatic moiety, hetero-aromatic moiety, amino moiety, acyl moiety, ester moiety, amide moiety, cyano moiety, nitro group, aryl moiety, tri-alkylsilyl moiety, tri-aryl silyl moiety.

2. The organometallic complex according to claim 1, wherein the atoms of the atomic groups of $Q^1$ and $Q^2$ are respectively selected from the group consisted of: C, N, P, O, S.

3. The organometallic complex according to claim 1, wherein the nitrogen-containing heterocyclic ring individually formed with $Q^1$ and $Q^2$ respectively further comprises at least one substituent selected from the group consisted of: hydrogen atom, halide atom, alkyl moiety, alkenyl moiety, halo-alkyl moiety, alkoxyl moiety, aromatic moiety, hetero-aromatic moiety, amino moiety, acyl moiety, ester moiety, amide moiety, cyano moiety, nitro group, aryl moiety.

4. The organometallic complex according to claim 1, wherein organometallic complex represented by the following formula:

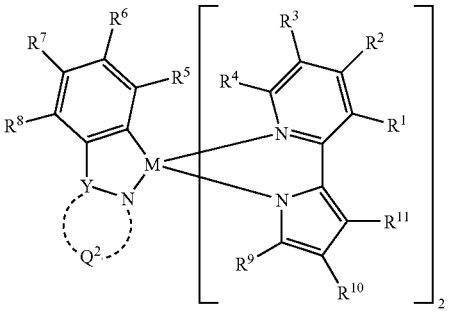

wherein $R^9$, $R^{10}$, and $R^{11}$ are identical or different, and $R^9$, $R^{10}$, and $R^{11}$ are respectively selected from the group consisting of a hydrogen atom, halide atom, alkyl moiety, alkenyl moiety, halo-alkyl moiety, alkoxyl moiety, aromatic moiety, hetero-aromatic moiety, amino moiety, acyl moiety, ester moiety, amide moiety, cyano moiety, nitro group, aryl moiety.

5. The organometallic complex according to claim 1, wherein organometallic complex represented by the following formula:

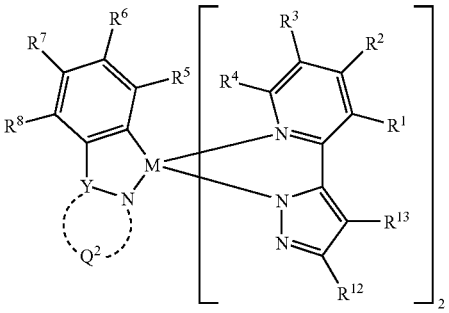

wherein $R^{12}$, and $R^{13}$ are identical or different, and $R^{12}$, and $R^{13}$ are respectively selected from the group consisting of a hydrogen atom, halide atom, alkyl moiety, alkenyl moiety, halo-alkyl moiety, alkoxyl moiety, aromatic moiety, hetero-aromatic moiety, amino moiety, acyl moiety, ester moiety, amide moiety, cyano moiety, nitro group, aryl moiety.

6. The organometallic complex according to claim 1, wherein organometallic complex represented by the following formula:

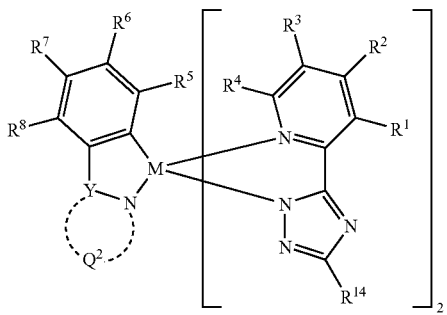

wherein $R^{14}$ is selected from the group consisting of a hydrogen atom, halide atom, alkyl moiety, alkenyl moiety, halo-alkyl moiety, alkoxyl moiety, aromatic moiety, hetero-aromatic moiety, amino moiety, acyl moiety, ester moiety, amide moiety, cyano moiety, nitro group, aryl moiety.

7. The organometallic complex according to claim 1, wherein organometallic complex represented by the following formula:

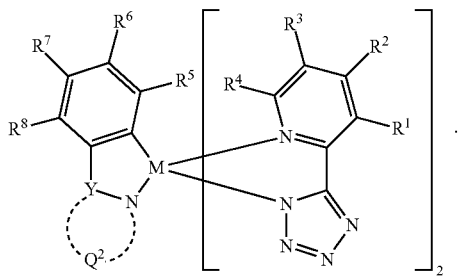

8. The organometallic complex according to claim 1, wherein the organometallic complex serves as a light-emitting material.

9. An organometallic complex represented by the following formula:

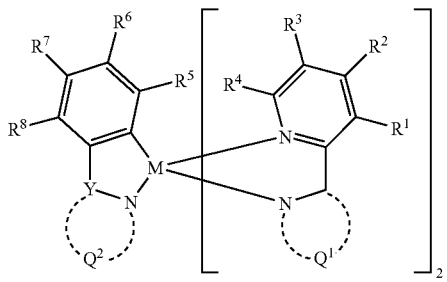

wherein M represents a transition metal selected from the group consisting of ruthenium, rhodium, tungsten, rhenium, osmium, iridium, and platinum; $Q^1$ and $Q^2$ respectively represent an atomic group forming a nitrogen-containing heterocyclic ring; at least one of $R^1$-$R^2$, $R^2$-$R^3$, $R^3$-$R^4$, $R^5$-$R^6$, $R^6$-$R^7$, and $R^7$-$R^8$ represent an atomic group forming a ring, wherein said ring is selected from the group consisted of aromatic ring, hetero-aromatic ring, cyclic alkene, and hetero-cyclic alkene, and the other substituents of $R^1$~$R^8$, wherein the substituents are not forming a ring, are identical or different, and respectively selected from the group consisting of a hydrogen atom, halide atom, alkyl moiety, alkenyl moiety, halo-alkyl moiety, alkoxyl moiety, aromatic moiety, hetero-aromatic moiety, amino moiety, acyl moiety, ester moiety, amide moiety, cyano moiety, nitro group, aryl moiety, tri-alkylsilyl moiety, tri-aryl silyl moiety.

10. The organometallic complex according to claim 9, wherein the atoms of the atomic group of $Q^1$ and $Q^2$ are respectively selected from the group consisted of: C, N, P, O, S.

11. The organometallic complex according to claim 9, wherein the nitrogen-containing heterocyclic ring respectively formed with $Q^1$ and $Q^2$ is respectively selected from the group consisted of: a five member ring, a six member ring, a seven member ring.

12. The organometallic complex according to claim 9, wherein the nitrogen-containing heterocyclic ring respectively formed with $Q^1$ and $Q^2$ respectively further comprises at least one substituent selected from the group consisted of: hydrogen atom, halide atom, alkyl moiety, alkenyl moiety, halo-alkyl moiety, alkoxyl moiety, aromatic moiety, hetero-aromatic moiety, amino moiety, acyl moiety, ester moiety, amide moiety, cyano moiety, nitro group, aryl moiety.

13. A light-emitting device comprising a pair of electrodes and one or more organic layers disposed between said electrodes, said one or more organic layers comprising a light-emitting layer, wherein at least one of said one or more organic layer comprises an organometallic complex represented by the following formula:

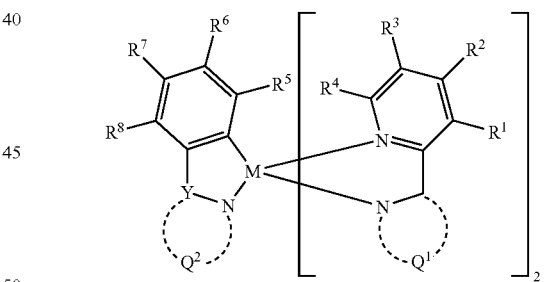

wherein M represents a transition metal selected from the group consisting of ruthenium, rhodium, tungsten, rhenium, osmium, iridium, and platinum; $Q^1$ and $Q^2$ respectively represent an atomic group forming a nitrogen-containing heterocyclic ring, wherein $Q^1$ is selected from the group consisted of: a five member ring, a seven member ring, wherein $Q^2$ is selected from the group consisted of: a five member ring, a six member ring, a seven member ring; Y is selected from the group consisted of C, and N; $R^1$, $R^2$, $R^3$, $R^4$, $R^5$, $R^6$, $R^7$, and $R^8$ are identical or different, and $R^1$, $R^2$, $R^3$, $R^4$, $R^5$, $R^6$, $R^7$, and $R^8$ are respectively selected from the group consisting of a hydrogen atom, halide atom, alkyl moiety, alkenyl moiety, halo-alkyl moiety, alkoxyl moiety, aromatic moiety, hetero-aromatic moiety, amino moiety, acyl moiety, ester moiety, amide moiety, cyano moiety, nitro group, aryl moiety, tri-alkylsilyl moiety, tri-aryl silyl moiety.

14. The light-emitting device according to claim 13, wherein the atoms of the atomic groups of $Q^1$ and $Q^2$ are respectively selected from the group consisted of: C, N, P, O, S.

15. The light-emitting device according to claim 13, wherein the nitrogen-containing heterocyclic rings respectively formed with $Q^1$ and $Q^2$ respectively further comprises at least one substituent selected from the group consisted of: hydrogen atom, halide atom, alkyl moiety, alkenyl moiety, halo-alkyl moiety, alkoxyl moiety, aromatic moiety, hetero-aromatic moiety, amino moiety, acyl moiety, ester moiety, amide moiety, cyano moiety, nitro group, aryl moiety.

16. The light-emitting device according to claim 13, wherein organometallic complex represented by the following formula:

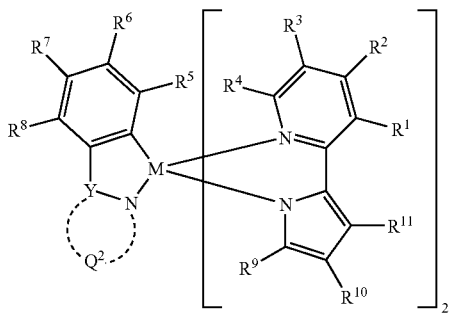

wherein $R^9$, $R^{10}$, and $R^{11}$ are identical or different, and $R^9$, $R^{10}$, and $R^{11}$ are respectively selected from the group consisting of a hydrogen atom, halide atom, alkyl moiety, alkenyl moiety, halo-alkyl moiety, alkoxyl moiety, aromatic moiety, hetero-aromatic moiety, amino moiety, acyl moiety, ester moiety, amide moiety, cyano moiety, nitro group, aryl moiety.

17. The light-emitting device according to claim 13, wherein organometallic complex represented by the following formula:

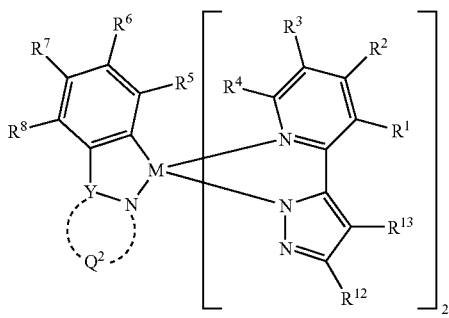

wherein $R^{12}$, and $R^{13}$ are identical or different, and $R^{12}$, and $R^{13}$ are respectively selected from the group consisting of a hydrogen atom, halide atom, alkyl moiety, alkenyl moiety, halo-alkyl moiety, alkoxyl moiety, aromatic moiety, hetero-aromatic moiety, amino moiety, acyl moiety, ester moiety, amide moiety, cyano moiety, nitro group, aryl moiety.

18. The light-emitting device according to claim 13, wherein organometallic complex represented by the following formula:

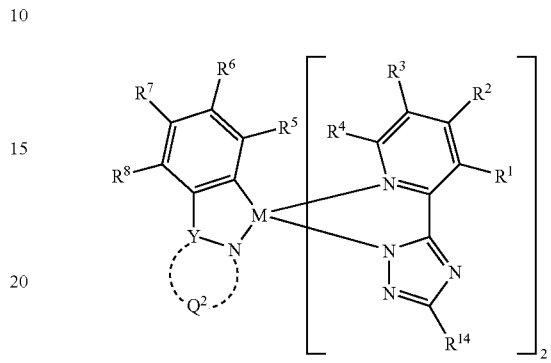

wherein $R^{14}$ is selected from the group consisting of a hydrogen atom, halide atom, alkyl moiety, alkenyl moiety, halo-alkyl moiety, alkoxyl moiety, aromatic moiety, hetero-aromatic moiety, amino moiety, acyl moiety, ester moiety, amide moiety, cyano moiety, nitro group, aryl moiety.

19. The light-emitting device according to claim 13, wherein organometallic complex represented by the following formula:

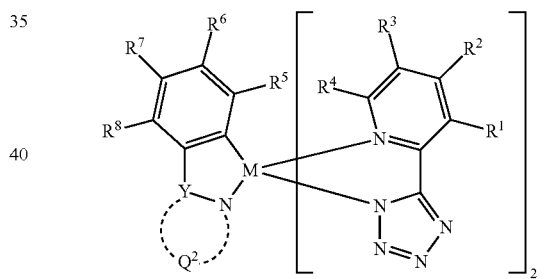

20. The light-emitting device according to claim 13, wherein M represents iridium.

21. The light-emitting device according to claim 13, wherein the organometallic complex serves as a light-emitting material.

22. The light-emitting device according to claim 13, wherein the organometallic complex serves as a host material.

* * * * *